(12) United States Patent
Smith et al.

(10) Patent No.: US 12,251,301 B2
(45) Date of Patent: Mar. 18, 2025

(54) EYELET INTERFERENCE SCREW AND METHODS OF USE

(71) Applicant: International Life Sciences, LLC, Marietta, GA (US)

(72) Inventors: Aaron Smith, Marietta, GA (US); Chase Thornburg, Cumming, GA (US); Jantzen Cole, Woodstock, GA (US)

(73) Assignee: International Life Sciences, LLC, Marietta, GA (US)

( * ) Notice: Subject to any disclaimer, the term of this patent is extended or adjusted under 35 U.S.C. 154(b) by 42 days.

(21) Appl. No.: 17/571,051

(22) Filed: Jan. 7, 2022

(65) Prior Publication Data
US 2022/0125573 A1 Apr. 28, 2022

Related U.S. Application Data

(63) Continuation of application No. 16/701,845, filed on Dec. 3, 2019, now abandoned.

(60) Provisional application No. 62/774,453, filed on Dec. 3, 2018.

(51) Int. Cl.
*A61F 2/08* (2006.01)
*A61B 17/04* (2006.01)
*A61F 2/00* (2006.01)

(52) U.S. Cl.
CPC ........ *A61F 2/0811* (2013.01); *A61B 17/0401* (2013.01); *A61B 2017/0409* (2013.01); *A61B 2017/0414* (2013.01); *A61B 2017/044* (2013.01); *A61F 2002/0081* (2013.01); *A61F 2002/0829* (2013.01); *A61F 2002/0852* (2013.01); *A61F 2002/0888* (2013.01)

(58) Field of Classification Search
CPC .......... A61B 17/12118; A61B 17/1615; A61B 17/1655; A61B 17/1714; A61B 2017/0409; A61B 2017/0414; A61B 2017/044; A61F 2/0811; A61F 2002/0081; A61F 2002/0829; A61F 2002/0852; A61F 2002/0858; A61F 2002/0888
See application file for complete search history.

(56) References Cited

U.S. PATENT DOCUMENTS

| | | | |
|---|---|---|---|
| 5,534,011 | A | 7/1996 | Greene, Jr. et al. |
| 5,964,783 | A | 10/1999 | Grafton et al. |
| 6,210,441 | B1 | 4/2001 | Flodin |
| 6,517,542 | B1 | 2/2003 | Papay et al. |
| 6,627,258 | B1 | 9/2003 | Flodin et al. |
| 6,666,877 | B2 | 12/2003 | Morgan et al. |
| 6,979,334 | B2 | 12/2005 | Dalton |
| 7,037,342 | B2 | 5/2006 | Nilsson et al. |

(Continued)

FOREIGN PATENT DOCUMENTS

WO 2002/030262 A2 4/2002

OTHER PUBLICATIONS

Non-Final Office Action, U.S. Appl. No. 16/701,845, filed Mar. 25, 2020, 13 pages.

(Continued)

*Primary Examiner* — Jocelin C Tanner
(74) *Attorney, Agent, or Firm* — Foley & Lardner LLP

(57) ABSTRACT

Provided herein are systems, methods and apparatuses for an eyelet interference screw and affixation of an implant to tissue employing the eyelet interference screw.

18 Claims, 9 Drawing Sheets

(56) References Cited

U.S. PATENT DOCUMENTS

| | | |
|---|---|---|
| 7,144,413 B2 | 12/2006 | Wilford et al. |
| 8,361,114 B2 | 1/2013 | Stone et al. |
| 8,764,797 B2 | 7/2014 | Dreyfuss et al. |
| 8,821,541 B2 | 9/2014 | Dreyfuss et al. |
| 8,845,685 B2 | 9/2014 | Stone et al. |
| 9,005,246 B2 | 4/2015 | Burkhart et al. |
| 9,089,415 B2 | 7/2015 | Brunelle et al. |
| 9,113,859 B2 | 8/2015 | Dooney, Jr. et al. |
| 9,179,907 B2 | 11/2015 | Elattrache et al. |
| 9,301,745 B2 | 4/2016 | Dreyfuss |
| 9,427,494 B2 | 8/2016 | Persson et al. |
| 9,486,207 B2 | 11/2016 | Dooney, Jr. et al. |
| 9,532,775 B2 | 1/2017 | Stone et al. |
| 9,861,353 B2 | 1/2018 | Feezor et al. |
| 9,980,753 B2 | 5/2018 | Jackson et al. |
| 10,155,067 B2 | 12/2018 | Persson et al. |
| 2001/0025181 A1 | 9/2001 | Freedlan |
| 2001/0053913 A1 | 12/2001 | Freedland |
| 2002/0156476 A1 | 10/2002 | Wilford |
| 2004/0093031 A1* | 5/2004 | Burkhart ............ A61B 17/0401 606/232 |
| 2009/0287246 A1 | 11/2009 | Cauldwell et al. |
| 2010/0088925 A1 | 4/2010 | Jia |
| 2010/0179592 A1 | 7/2010 | Martinek et al. |
| 2010/0249855 A1 | 9/2010 | Bless |
| 2010/0305576 A1 | 12/2010 | Ferguson et al. |
| 2010/0331896 A1* | 12/2010 | Le Couedic ....... A61B 17/0401 606/305 |
| 2011/0015735 A1 | 1/2011 | Persson |
| 2011/0107619 A1 | 5/2011 | Esquivel et al. |
| 2011/0319933 A1 | 12/2011 | Tepic |
| 2012/0041496 A1 | 2/2012 | Walker |
| 2012/0143250 A1 | 6/2012 | West, Jr. |
| 2012/0158051 A1 | 6/2012 | Foerster |
| 2013/0035721 A1* | 2/2013 | Brunelle ............ A61B 17/0401 606/232 |
| 2014/0243892 A1 | 8/2014 | Choinski |
| 2015/0018880 A1 | 1/2015 | Stone et al. |
| 2015/0245901 A1 | 9/2015 | Dougherty et al. |
| 2015/0313586 A1 | 11/2015 | Burkhart et al. |
| 2017/0151054 A1 | 6/2017 | Stone et al. |
| 2017/0209135 A1 | 7/2017 | Sullivan et al. |
| 2017/0209139 A1 | 7/2017 | Burkhart et al. |
| 2017/0231618 A1 | 8/2017 | Dreyfuss et al. |
| 2018/0230628 A1 | 8/2018 | Persson |
| 2018/0263617 A1 | 9/2018 | Feezor et al. |
| 2019/0062951 A1* | 2/2019 | Rizk .................... B29C 55/005 |
| 2019/0380692 A1* | 12/2019 | Brazil ................ A61B 17/0401 |

OTHER PUBLICATIONS

Final Office Action, U.S. Appl. No. 16/701,845, filed Sep. 24, 2020, 16 pages.

Non-Final Office Action, U.S. Appl. No. 16/701,845, filed Jun. 7, 2021, 17 pages.

Final Office Action, U.S. Appl. No. 16/701,845, filed Dec. 17, 2021, 7 pages.

International Search Report and Written Opinion, PCT Patent Application No. PCT/US19/064175, Feb. 14, 2020, 14 pages.

European Application No. 19894295.5, Extended European Search Report mailed on Aug. 8, 2022, 8 pages.

* cited by examiner

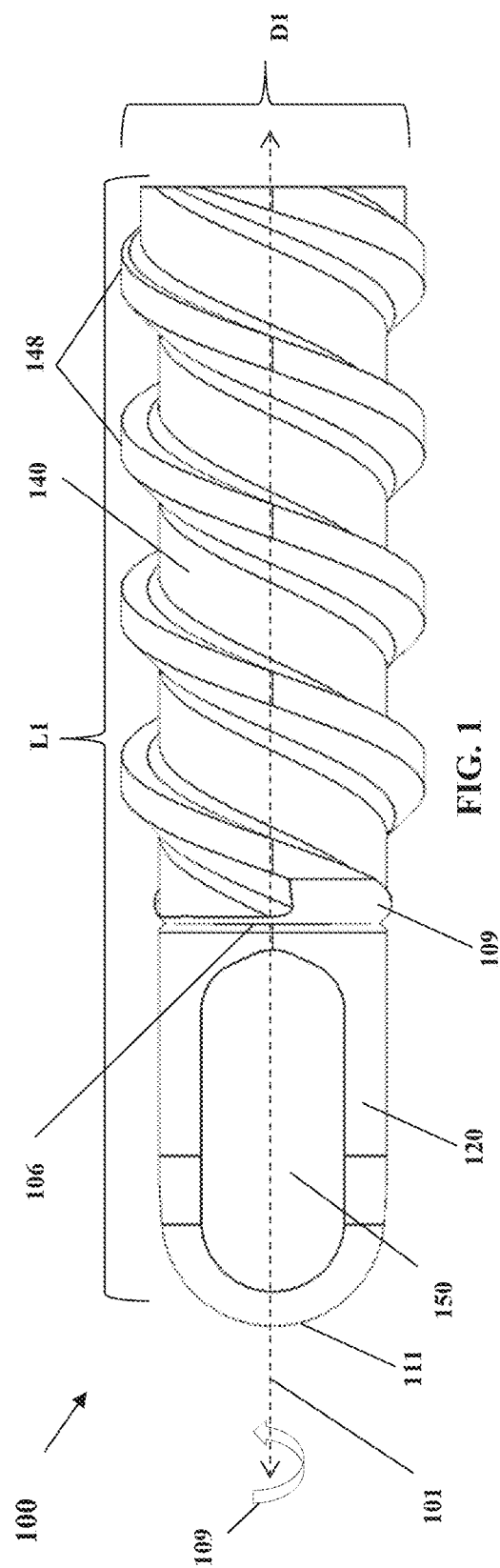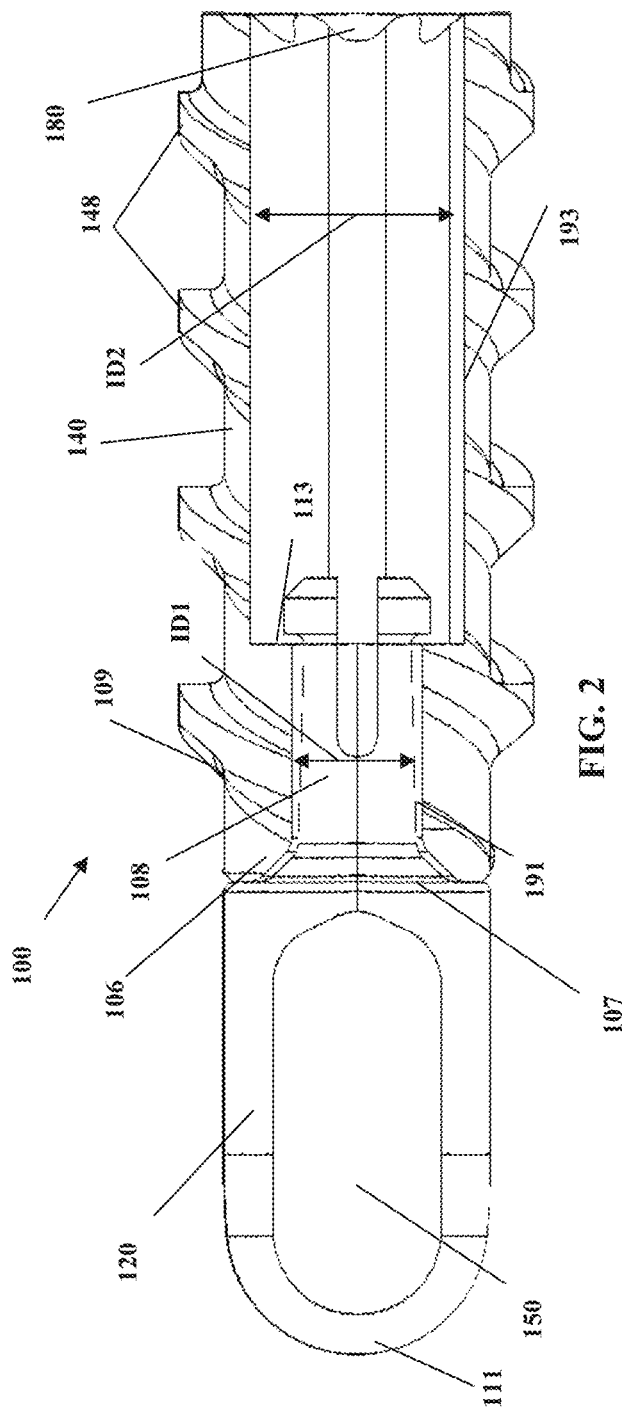

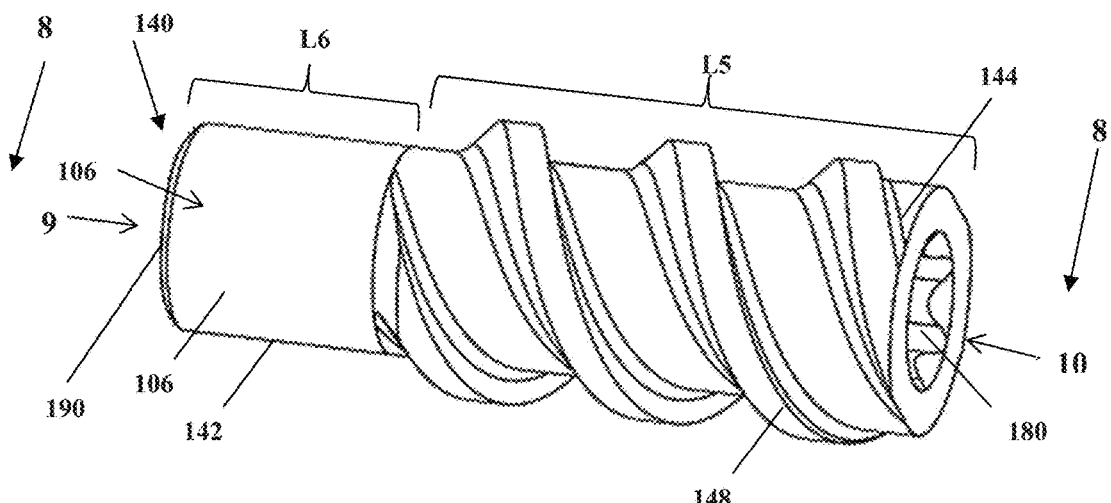
FIG. 7
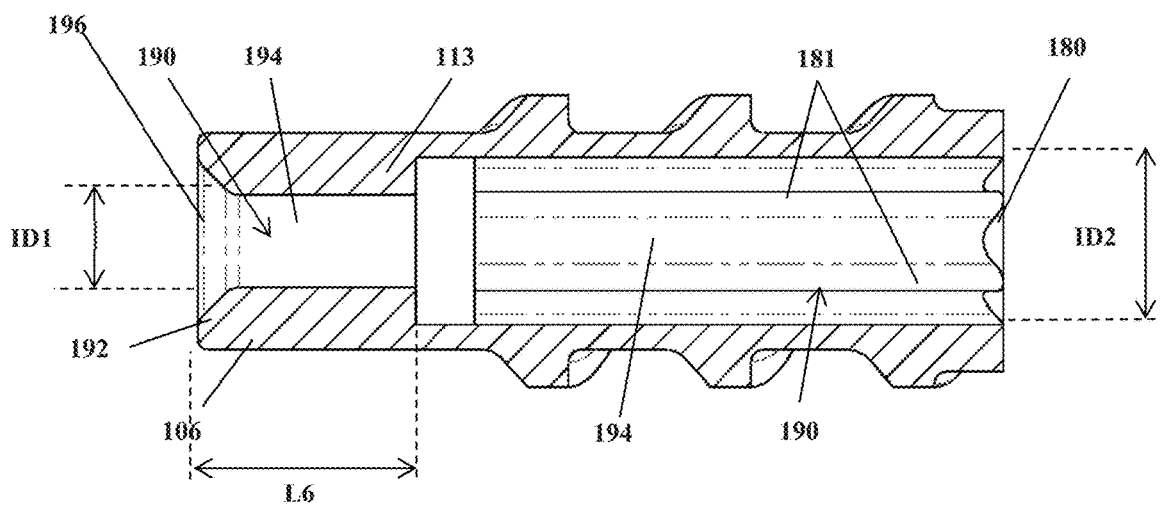
FIG. 8
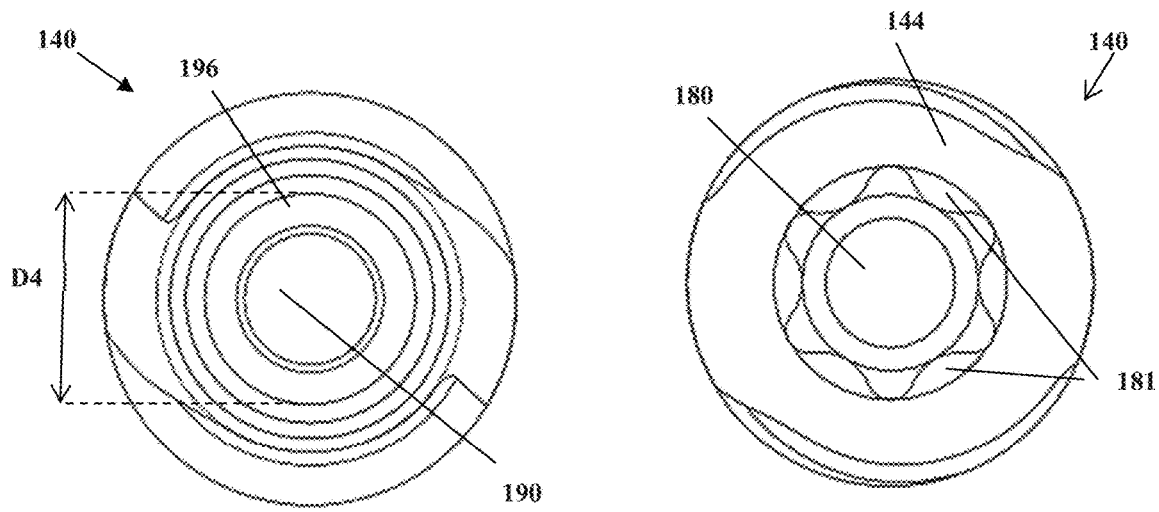
FIG. 9
FIG. 10

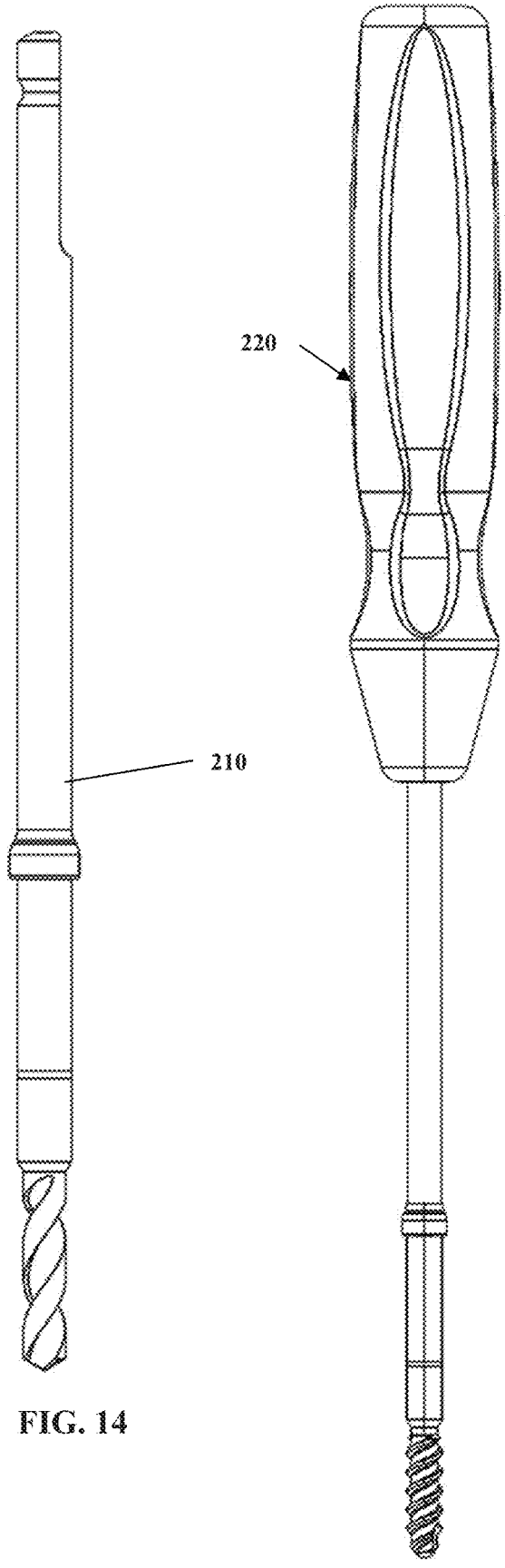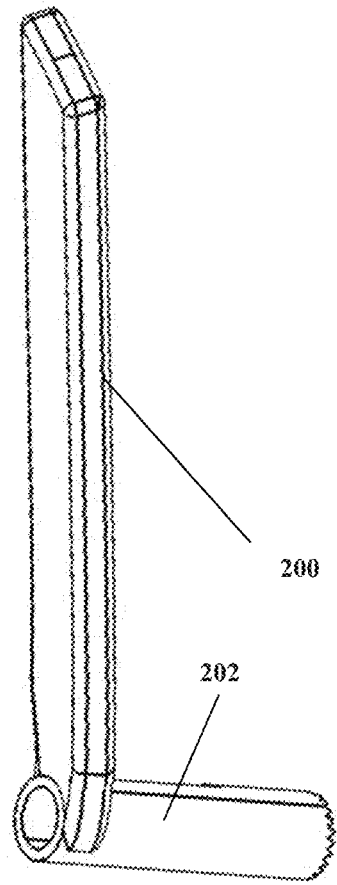
FIG. 14
FIG. 15
FIG. 16

EYELET INTERFERENCE SCREW AND METHODS OF USE

CROSS-REFERENCE TO RELATED APPLICATIONS

The present application is a continuation of U.S. patent application Ser. No. 16/701,845, filed Dec. 3, 2019, which claims priority to U.S. provisional application Ser. No. 62/774,453, filed Dec. 3, 2018, both of which are hereby incorporated by reference in their entirety.

BACKGROUND

The present invention relates generally to medical implants, medical kits, medical implant components or medical instruments. More particularly, the present invention relates to affixation devices configured to attach tissue, such as ligaments or tendons, to bone or muscle during surgical repair procedures.

Medical implants and instruments that are to be used in the human body and be in direct contact with the human tissues need to fulfill several requirements. Surgical treatment of injury to soft tissues of the musculoskeletal system of mammals caused by trauma, sudden overload, fatigue, disease or other degenerative medical condition may in some cases benefit from or even require structural support to start healing.

The present invention attempts to solve these problems as well as others.

SUMMARY OF THE INVENTION

Provided herein are systems, methods and apparatuses for an eyelet interference screw. An eyelet interference screw is disclosed herein and generally comprises a first end and a second end with a longitudinal axis extending from the first end to the second end. The first end is an eyelet member having an eyelet opening passing there through, and the second end is a threaded member configured to rotatably couple to the eyelet member, such that the eyelet member and the threaded member are able to rotate independently of each other about the longitudinal axis of the eyelet interference screw.

A method of implanting an eyelet interference screw is disclosed and comprises generally the steps of: forming a blind hole in the bone to which tissue is to be attached; loading an eyelet interference screw on a driver device, wherein a first end of an implant is attached to the opening on the eyelet interference screw; aligning the opening of the eyelet interference screw with the hole formed in the bone; seating the eyelet of the eyelet interference screw into the bone; rotating the driver to seat the eyelet interference screw into the bone until the proximal end of the eyelet interference screw is substantially flush with a surface of the bone and the implant is at least partially exposed outside the surface of the bone. A second end of an implant is then affixed in a manner like the first end of the implant.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

FIG. 1 is a side elevational view of an eyelet interference screw in accordance with an embodiment of the present invention.

FIG. 2 is a partial cross-sectional view taken along line 2-2 of FIG. 1.

FIG. 7 is a perspective view of a threaded member of the eyelet interference screw in accordance with one embodiment thereof.

FIG. 8 is a cross-sectional view taken along line 8-8 of FIG. 7.

FIG. 9 is an end elevational view taken along arrow 9 of FIG. 7.

FIG. 10 is an end elevational view taken along arrow 10 of FIG. 7.

FIG. 14 is a side view of a bone drill bit employed in the method of the present invention to form a blind hole in a bone into which the inventive eyelet interference screw is placed.

FIG. 15 is a side view of a tap device implanting the eyelet interference screw in accordance with the method of the present invention.

FIG. 16 is a perspective of a drill guide which may be employed to guide the bone drill and limit a depth of penetration of the bone drill into the bone in accordance with the method of the present invention.

DETAILED DESCRIPTION OF THE INVENTION

Figure 3:
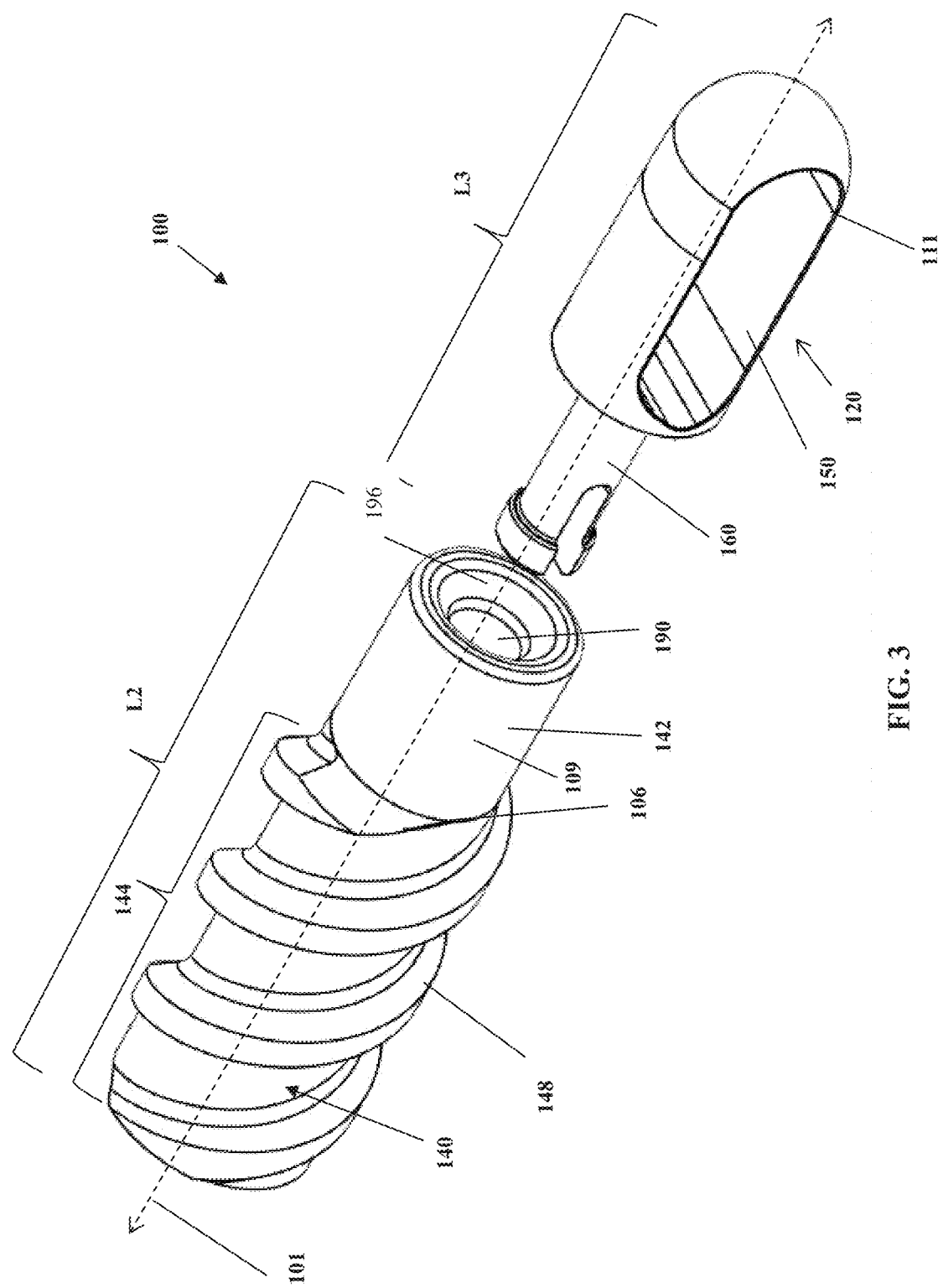
FIG. 3 is an exploded perspective view of an eyelet interference screw in accordance with the present invention.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Embodiments of the invention will be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

This application is intended to cover any variations, uses or adaptations of the invention following, in general, the principles of the invention, and including such. The foregoing and other features and advantages of the invention will become more apparent from the following detailed description of the exemplary embodiments, read in conjunction with the accompanying drawings. The detailed description and drawings are merely illustrative of the invention rather than limiting, the scope of the invention being defined by the appended claims and equivalents thereof.

For purposes of clarity, the following terms used in this patent application will have the following meanings:

The terminology used herein is for the purpose of describing example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the order discussed or illustrated, unless specifically identified as an order of performance. It is also to be understood that additional or alternative steps may be employed.

When an element or layer is referred to as being "on" "engaged" "connected," or "coupled" to or with another element, it may be directly on, engaged, connected or coupled to the other element or layer, or intervening elements or layers may be present. In contrast, when an element is referred to as being "directly on," "directly engaged to," "directly connected to, or "directly coupled to" or with another element or layer, there may be no intervening elements or layers present. Other words used to describe the relationship between elements should be interpreted in a like fashion (e.g., "between" versus "directly between," "adjacent" versus directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below", or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

"Substantially" is intended to mean a quantity, property, or value that is present to a great or significant extent and less than, more than or equal to totally. For example, substantially vertical may bean less than greater than or equal to completely vertical.

"About" is intended to mean a quantity, property, or value that is present at ±10%. Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of all values and further divided ranges within the entire range, including endpoints given for the ranges.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Recitation of ranges of values herein are merely intended to serve as a shorthand method of referring individually to each separate value falling within the recited range, unless otherwise indicated herein, and each separate value is incorporated into the specification as if it were individually recited herein.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

As used herein, the terms "blind hole" and "hole" when used to describe a hole drilled into bone tissue refers to a hold that is open to the bone tissue at one end, does not pass through the bone tissue and is closed by bone tissue at an opposing end of the hole.

As used herein, the terms "thread," "threads," or "threaded" is intended to include protuberances forming a continuous helical thread, discontinuous helical threads, or circumferential ring structures, unless the context expresses unequivocally otherwise.

The inventive eyelet interference screw may be used to treat a tendon or ligament repair. The instrument may include an implantation device to secure the implant into bone or a tissue, such as a bone screw, staple, and the like. Sutures may further secure the implant to the ligament, tendon, or bone screw. Surgical kits may be produced containing elements necessary for treating and/or repairing tendons and ligaments with the implant. Such a kit may include various configurations of the implant. One or more surgical tools used in tendon and/or ligament repair surgery are also advantageously provided in such kits. The surgical kits may treat the following tissue, ligaments, and tendons including, but are not limited to a lateral ankle anterior talofibular ligament (ATFL); calcaneofibular ligament (CFL); medial collateral ligament (MCL), plantar plate, Achilles tendon, peroneal tendon, medial ankle (spring ligament, deltoid ligament), syndesmosis, open rotator cuff, acromioclavicular joint kit (AC Joint), and the anterior collateral ligament (ACL).

Generally speaking, inventive eyelet interference screw may be used to attach a tendon or ligament repair implant, which may include the materials, configuration, or properties as described in U.S. Pat. Nos. 6,210.441, 6,627,258, 7,037,342, 9,427,494, 10,155,067, and/or U.S. Patent Application Publications US 2011/0015735 or US 2018-0230628, herein incorporated by reference in their entries. The repair implant, itself, may be a FLEXBAND, FLEXBAND PLUS or FLEXPATCH (Artelon, Marietta, Georgia USA). Such types of repair implants may be referred to synonymously herein as a mesh strip.

Referring now to FIGS. 1-3 the eyelet interference screw 100 generally comprises an externally threaded member 109 and an eyelet member portion 111. The eyelet interference screw 100 has a length L1 and a longitudinal axis 101. The eyelet member portion 111 generally comprises an eyelet member 120 having an eyelet opening 150 passing through the eyelet member 120, and a seating projection 108. Seating projection 108 projects outwardly from the eyelet member 120 along the longitudinal axis 101. The eyelet member 120 and the eyelet opening 150 may collectively or independently be configured to any desirable shape, including, without limitation, generally circular, generally elliptical, generally oval, generally square, or generally rectangular. The seating projection 108 is, according to one embodiment, a generally cylindrical member, and according to other embodiments, may have alternative configurations, such as cubic, rectilinear, polygonal or the like. The seating projection will preferably have smaller cross-sectional dimension than the eyelet member 120 and will preferably have a tapered section 107 extending from a relatively larger aspect at its junction with the eyelet member 120 to a relatively smaller aspect at its junction with the seating projection 108.

As further illustrated in FIGS. 1-3, the threaded member 109 of the eyelet interference screw 100 includes a central core member 140 having at least one protuberance, for example, external helical thread 148 surrounding at least a longitudinal aspect of the central core member 140. The central core member 140 is a generally tubular member having a central bore 190 passing through a longitudinal axis thereof. Central bore 190 preferably has a first end section 191 having an inner diameter ID1 and terminating in a receiving opening 196 which receives the eyelet member 120 therethrough. Central bore 190 also has a second end section 193 having inner diameter ID2, where ID2 is relatively larger than ID1 A flange 113 is provided in the central core member 140 at the transition between ID1 and ID2 of the central bore 190.

To secure the seating projection 108 within the central bore 190 of the central core member 140, multiple configurations may be employed that couple the eyelet member portion 111 to the threaded member 109 and allow rotation of the eyelet member portion 111 relative to the threaded member 109. Without intending to be limited to the specific embodiment illustrated, one example of a suitable one-way coupling is to provide split legs 117 extending from the seating projection 108, each of the split legs 117 having at least one pawl 115. In this configuration, each of the split legs 117 act as a spring and are compressed as the seating projection 108 is passed into and through the proximal section of the central bore 190. Upon entering the enlarged distal section of the central bore 190, the split legs 117 return to their normal non-tensioned position extending radially outward and radially extending pawl engages the flange 113 within the central bore 190. In this manner, the eyelet member portion 111 is coupled to the threaded member.

According to one embodiment, the eyelet member portion 111 is configured to couple to and rotatably engage with the threaded member 109 in such a manner that allows the threaded member 109 to rotate about the longitudinal axis 101 when the threaded member 109 and the eyelet member portion 111 are engaged.

The eyelet member portion 111 may be rotatably coupled within the proximal portion of central bore 190 and along the longitudinal axis 101 of the eyelet interference screw 100. The force required to rotate the eyelet member portion 111 may be determined by the relative tolerances between the outer diameter of the seating projection 108 and the ID1 and ID2 of the central bore. Alternatively, there may be provided interference means for limiting the rotational force needed to rotate the eyelet member portion 111 relative to the seating projection 108. Such alternative interference means may include, for example, a ratchet mechanism, detents, or other interference mechanisms provided within the central bore 190 to limit or control the force required to rotate the eyelet member portion 111 relative to the threaded member 109. Rotational forces for the eyelet member portion may be between about 1 in/lb (0.11 N/m) and about 20 in/lb (2.26 N/m). Alternatively, the eyelet member portion 111 may be configured to be in a fixed, non-rotatable position, relative to the threaded member 109 and not rotate about the longitudinal axis 101 of the eyelet interference screw.

In one embodiment, the eyelet interference screw 100 has an outer diameter D1, as shown in FIG. 1. In one embodiment, the diameter D1 and length L1 may be varied based upon the surgical procedure, implant to be affixed and/or tissue being repaired. As a non-limiting example only, D1 may be within the range of about 2.5 mm to about 10.5 mm and length L1 may be within range of about 8 mm to about 35 mm. The eyelet member 120 includes a length L3 and the threaded member includes a length L2. When eyelet member 120 is coupled to threaded member 109 the overall length of the eyelet interference screw 100 is length L1, as depicted in FIG. 3.

In one embodiment, as shown in FIGS. 4A-6, the eyelet member portion 111 has a first end 122 and a second end 124, as shown in the respective end views depicted in FIGS. 4A-6. The second end 124 includes a connector projection 160 and the first end 122 includes the eyelet member 120 and the eyelet opening 150. Eyelet opening 150 is configured to allow for joining sutures and/or an implant passing through the eyelet opening 150 and secured to the eyelet member 120. The eyelet opening 150 is configured to have a length L4 and width W4, which are each are optionally dimensioned to allow for sutures and/or an implant to be secured to the eyelet opening 150 and the eyelet member 120. In one embodiment, the length L4 and width W4 of the eyelet opening 150 is optimized for a particular surgical procedure, implant, or tissue location, where the length L4 and/or width W4 may be greater or lesser due to the nature of the surgical location, ligament, tissue and the like. In one embodiment, the diameters D4 are between about 3.0 mm to about 7.0 mm and the length L4 is between 4.0 mm and about 10.0 mm.

The eyelet member 120 has a first end 158 and a second end 154. First end 158 of eyelet member 120 may have a curved or rounded configuration to facilitate insertion of the eyelet interference screw 100 into the blind hole 99. The second end 154 of the eyelet member 120 is adjacent to and abuts the connector projection 160. The eyelet opening 150 may have a variety of shapes, including, for example, circular, oval, elliptical, polygonal, hexagonal, a locking V-notch, or the like. An eyelet opening 150 having a generally oval shape is depicted in FIG. 4A, whereas, an eyelet opening 150 having a V-notch 156 is depicted in FIG. 4B.

Figure 6:
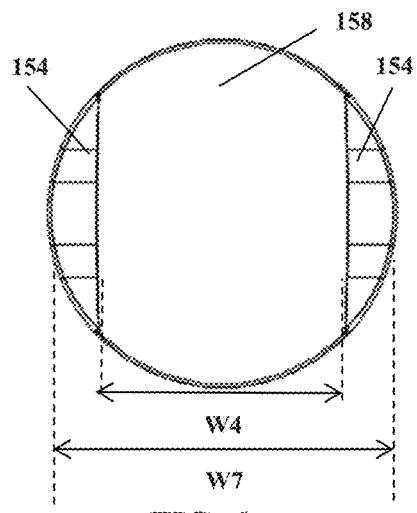
FIG. 6 is an end view taken along arrow 6 of FIG. 4B.

The second end 154 has a width W7 that is greater than a width W4 of the first end 158 of the eyelet member 120, as depicted in FIG. 6. The difference between W4 and W7 provides space for a suture or implant to extend outward from blind hole 99 once the eyelet interference screw 100 is fully placed in the blind hole 99.

Figure 4A:
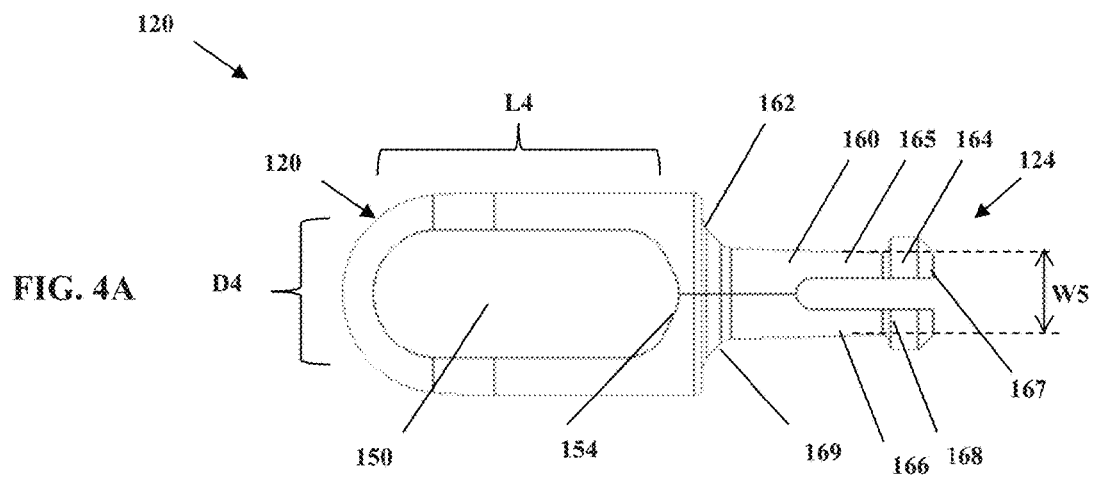
FIG. 4A is a side elevational view of an eyelet member in accordance with an embodiment of the present invention.
Figure 4B:
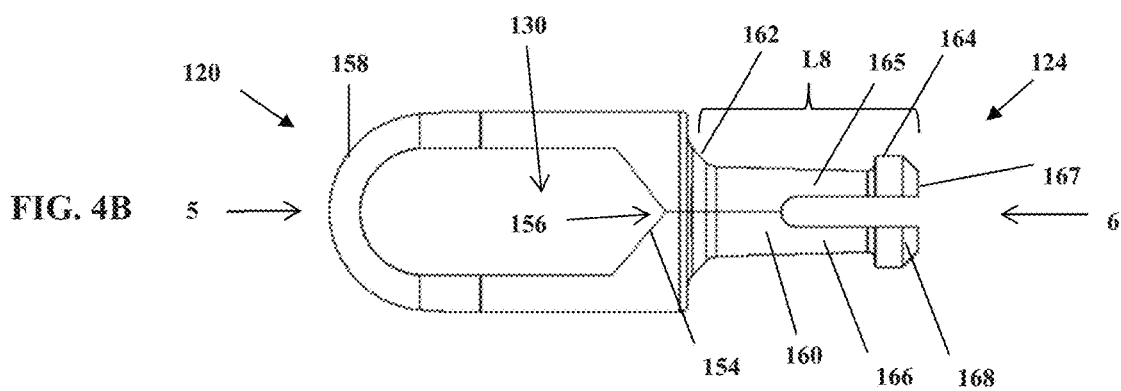
FIG. 4B is a side elevational view of an eyelet member in accordance with an alternative embodiment of the present invention.

As shown in FIGS. 4A-4B, the connector projection 160 includes a first section 162 that joins the connector projection 160 to the eyelet member 120 and a section 164 that extends from the first portion 162. The second section 164 includes at least one of a plurality of legs 165, 166, and may include a first leg 165 and a second leg 166 that flex or transpose inward towards a slot gap when operably disposed with the central core member 140. The connector projection 160 is generally coaxial and concentric with the threaded member 109 to allow for rotation within the central bore central about the longitudinal axis. In another embodiment, the snap fit extension includes a plurality of legs, such that there is a first leg, a second leg, and a third leg that flex inwards or transpose inward towards a gap when operably disposed with the central core member 140. In another embodiment, the snap fit extension includes a plurality of legs, such that there is a first leg, a second leg, a third leg, and a fourth leg that flex inwards or transpose inward towards a gap when operably disposed with the central core member 140.

Figure 5:
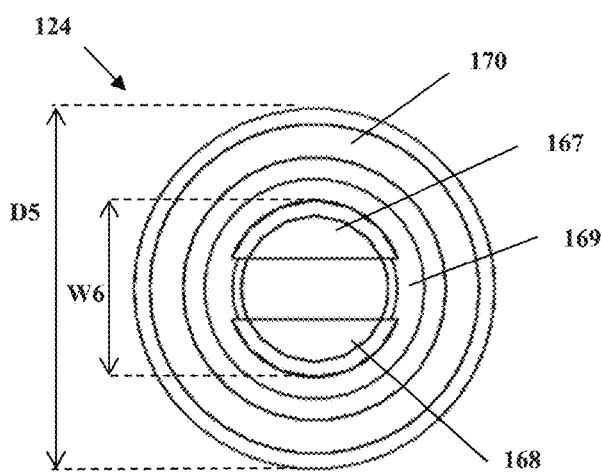
FIG. 5 is an end view taken along arrow 5 of FIG. 4B.

As shown in FIG. 4B, the connector projection 160 has a length L8 configured to pass through the at least a portion of the central bore 190 of threaded member 109. The first leg 165 includes a first pawl 167 and the second leg 166 includes a second pawl 168 to seat within the threaded member and prevent distal movement of the eyelet member 120 during operation. The first pawl 167 and the second pawl 168 define a diameter W6, as shown in FIG. 5. In alternative embodiments, the second section 164 may include other extensions and connections, such as a threaded, sealed, or bracketed connection. The first section 162 includes a curvilinear section 169 to permit the eyelet member 120 to swivel about the longitudinal axis of the eyelet interference screw.

As shown in FIGS. 7-8, the central core member 140 has an unthreaded section 142 and an externally threaded section 144. The central bore 190 of the externally threaded section 144 terminates in a driver coupling opening 180 and, as illustrated in FIG. 8, the central bore 190 within the unthreaded section 142 terminates in a receiving opening 196. Driver coupling opening 180 is configured to receive a driver for applying torsional or linear forces to the threaded member 109. In one embodiment, the central bore 190 includes a plurality of splines 181 on an inner surface of central bore 190 in the externally threaded section 144. The plurality of splines operably engage with the driver.

The threaded member 109 of the eyelet interference screw includes at least one external helical thread 148 on the outer surface of the central core member 140. The at least one external helical thread 148 may be a single continuous helical thread or may be plural discontinuous threads. A thread pitch, or the distance between adjacent helical rings of the at least one external helical thread 148, may be uniform or may be non-uniform. The at least one external helical thread 148 may extend along a substantial longitudinal extent of the threaded member 109, as depicted in FIGS. 1-3, or may extend along only a portion of the longitudinal extend of the threaded member 109, as depicted in FIGS. 7-8. In the later instance, an unthreaded section 142 of the central core member 140 of threaded member 109 will be present. In either instance, the length L5 of the at least one external helical thread 148 is preferably at least two times the helical pitch of the threaded member 109.

As shown in FIGS. 7-8, the first end section 191 of central bore 190 may, optionally, have an inward taper 192 to receiving opening 196. Inward taper 192 tapers toward central bore 190 and has a relatively larger diameter at its outermost aspect than ID1 of the first end section 191 central bore 190. When employed, the inward taper 192 facilitates engaging the connector projection 160 of the eyelet member 120 with central bore 190.

In accordance with the embodiment depicted in FIGS. 7-10, the unthreaded section 142 of threaded member 109 has a length L6. Length L6 may be between about 0.10 mm and about 45.0 mm and is selected based upon the implant to be employed in a surgical procedure. It will be understood that the longer the length L6, the larger the unthreaded surface area will be provided for the eyelet interference screw 100.

As shown in FIGS. 7-10, and as discussed above with reference to FIGS. 1-3, central bore 190 has the first end section 191 that opens to the receiving opening 196 and the second end section 193 that opens to the driver coupling opening 180. Driver coupling opening 180 is configured to accept and couple to a driver, as will be discussed hereinafter with reference to FIGS. 13A-16, which is employed in the method of the present invention to place and seat the eyelet interference screw 100 in the blind hole 99. As previously discussed, the receiving opening 196, receives the connector projection 160 of the eyelet member 120 therethrough to operably couple the eyelet member 120 to the threaded member 109. The receiving opening 196 may be tapered inward to mate with a corresponding taper of the first section 162 of the connector projection 160 with the eyelet member 120 and the threaded member 109 are coupled to each other.

Figure 11:
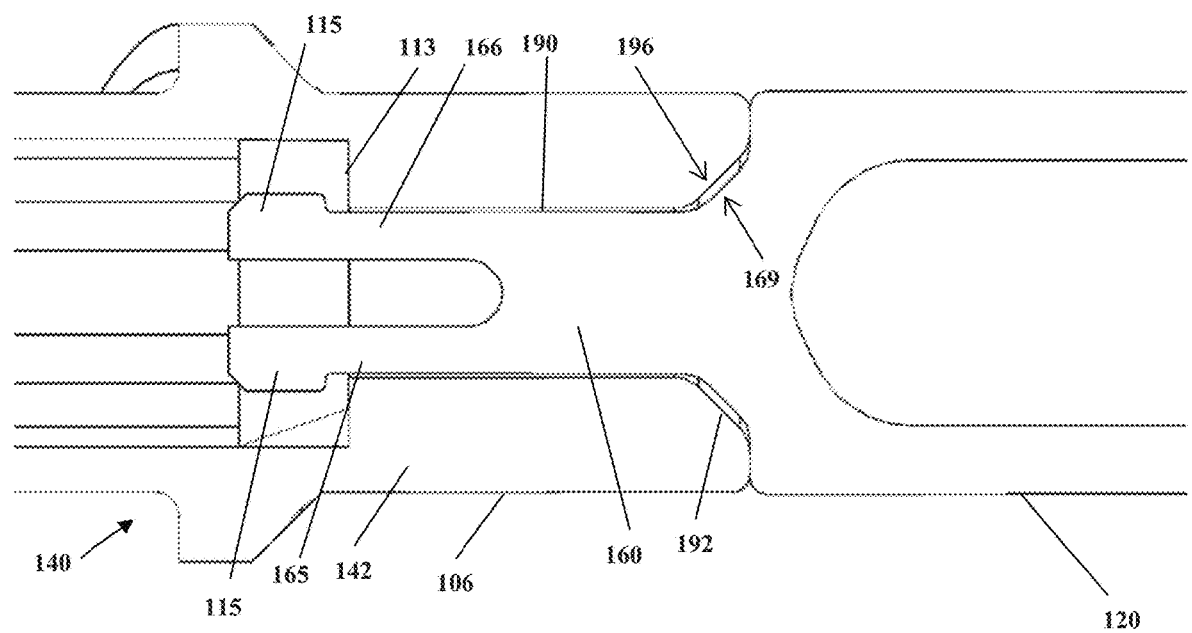
FIG. 11 is fragmentary cross-sectional view illustrating engagement of the eyelet portion with the threaded member of an eyelet interference screw in accordance with an embodiment of the present invention.

FIG. 11 depicts a magnified view of connector projection 160 fully engaged within first end section 191 of central bore 190. Tapered receiving opening 196 mates with the taper of first portion 162, and connector projection 160 extends through first end section 191 of central bore 190 such that the legs 117 of connector projection 160 pass into the second end section 193 of the central bore 190 and at least one pawl 115 seat against flange 113 to secure the eyelet member 120 to the threaded member 109.

Figure 12:
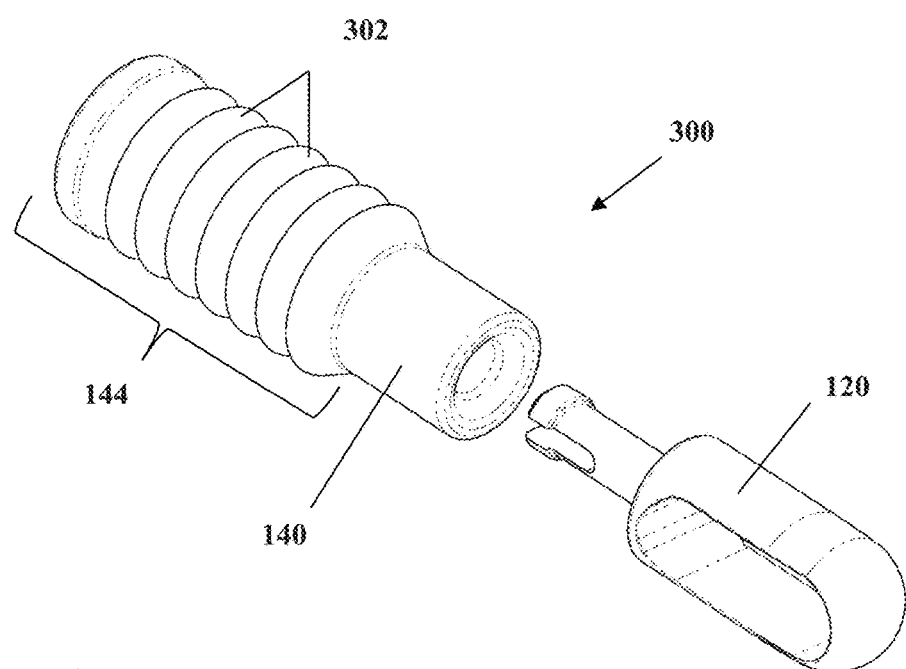
FIG. 12 is a perspective exploded view of an alternative embodiment of an eyelet interference screw in accordance with the present invention.

FIG. 12 depicts an alternative eyelet interference screw 300. Eyelet interference screw 300 is like eyelet interference screw 100, except that the external helical thread 148 on the threaded section 144 of the eyelet interference screw 100 is replaced with at least one circumferential ring 302 or plural adjacent circumferential rings 302 that project radially outward from the surface of the central core member 140. Circumferential rings 302 may have a wide variety of configurations, for example, circumferential rings 302 may canted toward the driver opening 180 to facilitate insertion of the eyelet interference screw 300 into the blind hole 99 and also provide resistance to withdrawal of the eyelet interference screw 300 from the blind hole 99 once fully inserted. Circumferential rings 302 may also be radially extending substantially perpendicular to the longitudinal axis of the eyelet interference screw. The extent to which circumferential rings project from the central core member 140 may be determined by a number of non-exclusive factors, including, for example, the pliability or compliance desired for the circumferential rings, the match with the diameter of the blind hole 99, the degree of resistance force desired to insert or withdraw the eyelet interference screw 300 into or from the blind hole 99, respectively, or the anchoring force desired for the eyelet interference screw 300.

It will also be appreciated that the threaded section 144 of eyelet interference screw 100, 300 may external helical threads 148, circumferential rings 302, or combinations of external helical threads 148 and circumferential rings 302 along different longitudinal regions of the threaded section 144.

In one embodiment, the eyelet interference screw eliminates transosseous tunnels in tendon repairs and ligament reconstructions by simplifying tissue fixation in a bone socket while maintaining tension of the tissue throughout fixation.

The eyelet interference screw comprises an increased initial fixation strength, thereby decreasing the risk of early failure during rehabilitation for any implant or interference screw.

Alternative sizes and configurations of the inventive eyelet interference screw are contemplated by the present invention and may be employed depending upon the tissue, tendon, or ligament to be repaired. Implants which may be employed with the eyelet interference screw 100 may have a wide variety of dimensions, including, for example about 3 cm×about 4 cm, about 4 cm×about 6 cm, and about 6 cm×about 9 cm, about 0.3 cm×about 8.0 cm, about 0.3 cm×about 16 cm, about 0.3×32 cm, about 0.5 cm×about 8.0 cm, about 0.5 cm×about 16 cm, about 0.7 cm×about 8 cm, about 0.7 cm×about 16 cm, about 0.7 cm×about 32 cm, about 0.5 cm×about 32 cm. The implants may have a generally cylindrical, generally tubular, or generally planar configuration. The implant itself may have thickness between about 0.5 mm and about 1.5 mm. The implant may have a modulus of elasticity between about 12 Mpa and about 16 Mpa, alternatively between about 12 Mpa and about 116 Mpa. The modulus of elasticity may be selected according to the tissue, tendon, or ligament being treated.

Instruments useful in the method of the present invention to fix the eyelet interference screw 100 to tissue are shown in FIGS. 14-16. A drill bit 210 and tap 220 are employed create and prepare the hole 99 in the bone. The eyelet interference screw 100 is either loaded or preloaded on the driver 230. The implant 240 and sutures 232 are joined to the eyelet member 120, either before or after loading the eyelet interference screw 100 onto the driver 230. The driver 230 couples to the eyelet interference screw 100 at the driver coupling opening 180 of the threaded member 109. As shown in FIGS. 13A-13D, the eyelet member 120, having the implant 240 and sutures 232 joined thereto, is introduced into the blind hole 99 and the eyelet interference screw is then inserted into the blind hole 99 using the driver 230 until the at least one external thread 148 on the central core member 140 engage with the bone tissue surrounding the blind hole 99. The driver 230 is then rotated to screw the threaded member 109 into the bone hole and drive the eyelet member 120 further into the blind hole 99, with the implant 240 and sutures 232 extending along the length L1 of the eyelet interference screw 100 and projecting out of the blind hole 99.

It will be understood by those skilled in the art, that a wide variety of drill bits, including different diameters, lengths, and configurations may be employed, as is well known in the orthopedic field, to create different dimensions for blind hole 99.

In one embodiment, the drill bit 210 employed for drilling into the bone tissue to create the blind hole 99. Optionally, a guidewire may be used for guiding the drill during drilling the blind hole 99. The tap 220 allows for precise tapping near the bone. As shown in FIG. 15, a drill guide 200 having a drill collar 202 may be used to delimit the depth of drilling and define a depth of the blind hole 99. A wide variety of drill guides 200 are well known in the art, and, in addition to a stop collar-type drill guide, there are also drill stop collars that removably attach to drill bits to delimit the depth of drilling to form the blind hole 99 in the bone tissue.

A driver or other tensioning device is used to tamp and/or thread the implant into the bone, according to one embodiment. The driver may be any configuration suitable for applying a rotary force to the eyelet interference screw, including, without limitation, slotted, cruciform, internal polygon, hexalobular, three-pointed or other. Slotted drivers include a slot drive and a cross drive type. Cruciform drive types include, for example Phillips, Frearson, French recess, mortorq, torq-set, or the like. Internal polygon driver types include, for example, tri-angle, double square, Robertson, triple-square, hex socket or Allen, 12-spline flange, security hex or double hex. Hexalobular driver types include, for example, torx, line head, or polydrive. Three-pointed driver types include, for example, tri-point, tri-wing or tri-groove.

Figure 13A:
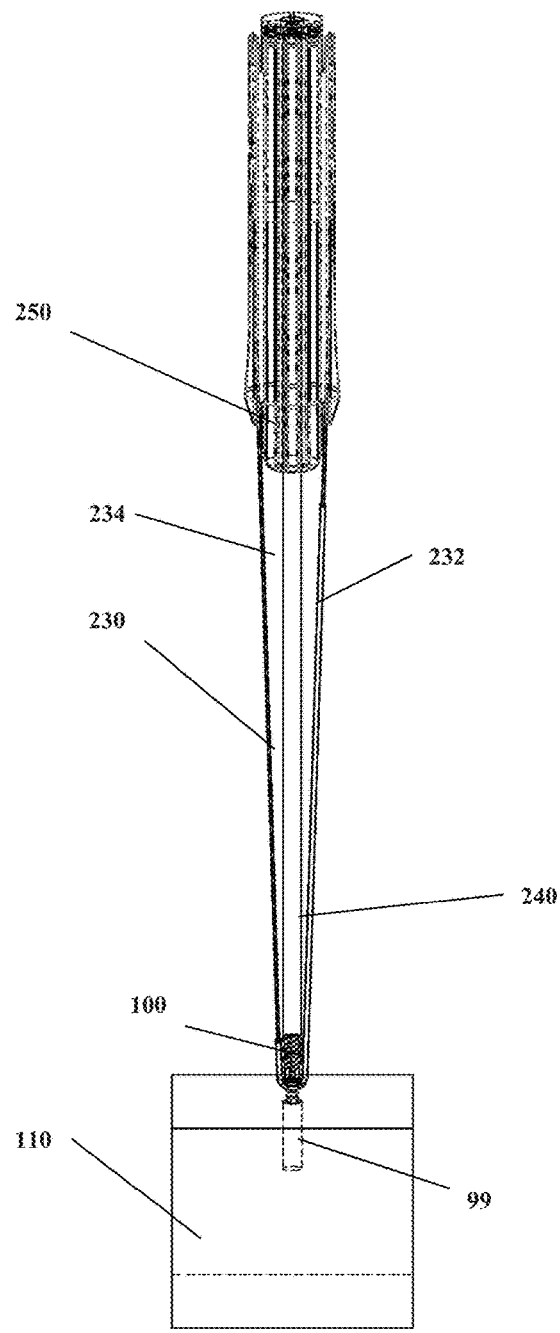
FIG. 13A is a side elevational view of a loading device for implanting the inventive eyelet interference screw into bone in accordance with the present invention.
Figure 13B:
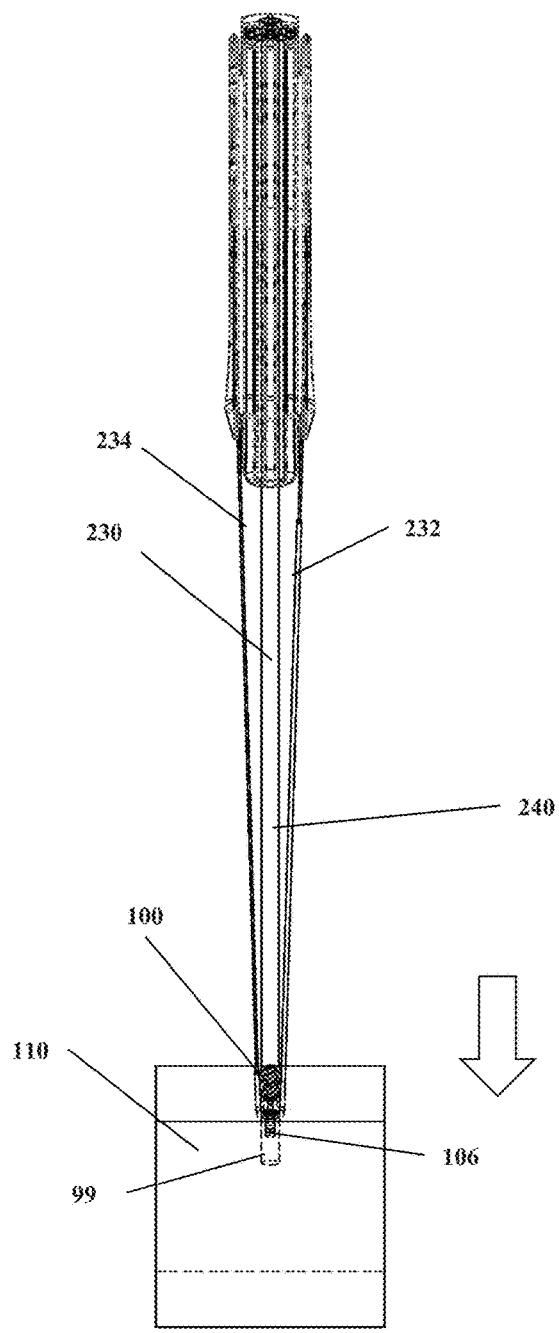
FIG. 13B is a side elevational view the loading device for implanting the inventive eyelet interference screw diagrammatically illustrating the eyelet interference screw being implanted into bone in accordance with the present invention.
Figure 13C:
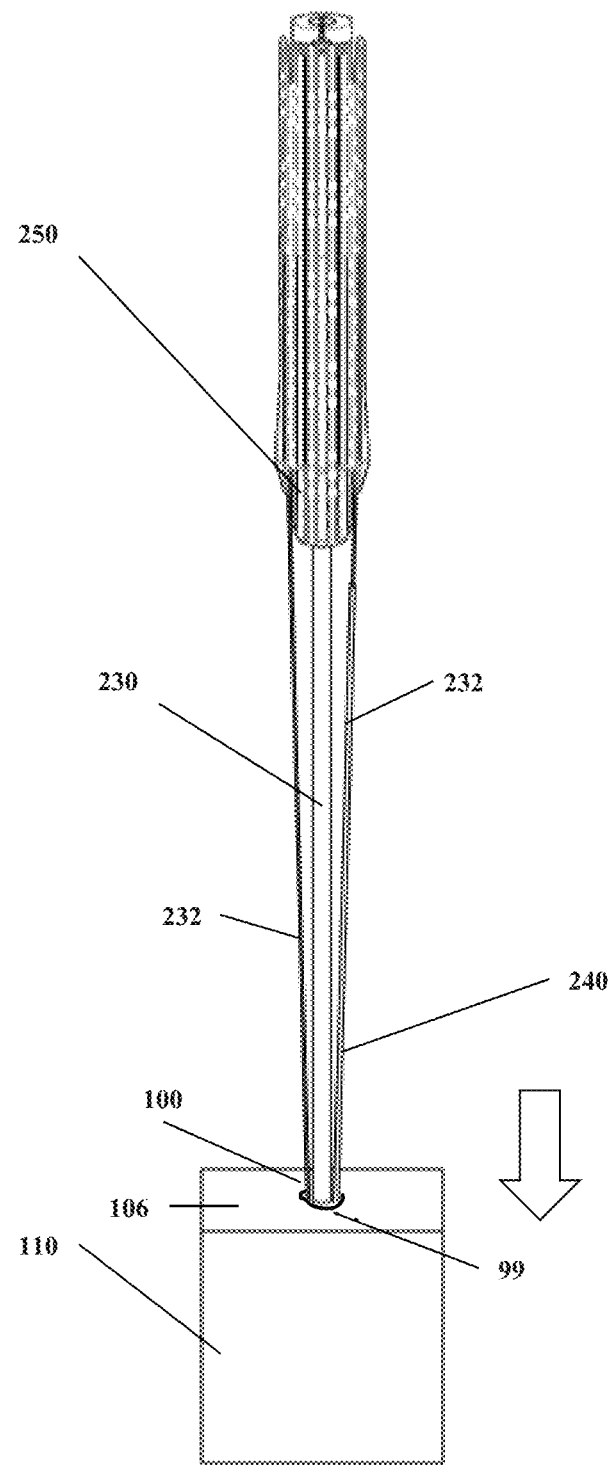
FIG. 13C is a side elevational view of the loading device for implanting the inventive eyelet interference screw diagrammatically illustrating the eyelet interference screw fully implanted into bone in accordance with the present invention.
Figure 13D:
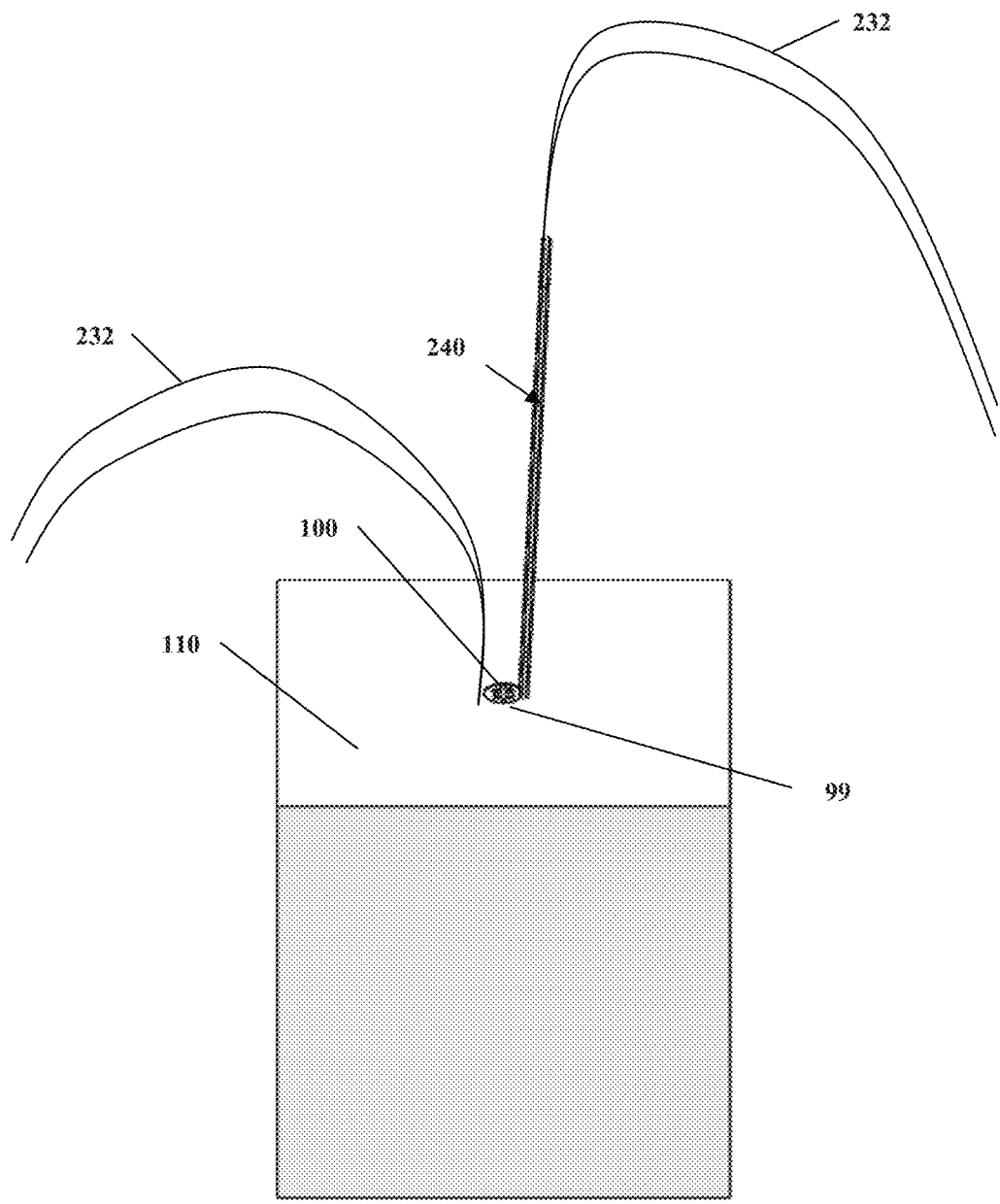
FIG. 13D is a diagrammatic view of a bone having the inventive eyelet interference screw implanted in the bone and a tissue repair implant extending from the eyelet interference screw external to the bone.

With the eyelet of the eyelet interference screw 100 coaxially aligned with the blind hole 99, a mallet or other suitable tamping driver may be used to insert and seat the eyelet of the eyelet interference screw 100 into the blind hole 99 until seated at the threaded interface 106, as shown in FIG. 13C. Once seated at the threaded interface 106, the driver handle 250 may either be rotated to thread the eyelet interference screw 100 into the bone 110 or continued to be malleted to drive the eyelet interference screw 100 into the bone 110. The sutures 232 and the implant 240 coupled to the eyelet member 120 are pushed into the blind hole 99 as the eyelet interference screw 100 is tamped and/or screwed into the blind hole 99. A second end of the sutures 232 and the implant 240, which is to be affixed to a secondary eyelet interference screws 100, remain either within or external to the driver. The screwdriver 130 is used to drive the threaded member 109 of the eyelet interference screw 100 until it is flush with the surface of the bone, as shown in FIG. 13C. The final step is to remove driver 230 leaving behind the eyelet interference screw 100 and implant 240 with sutures 232, as shown in FIG. 13D. To complete the procedure, create and prepare a second blind hole 99 as described above. Thread the free end of the implant 240 through the eyelet of a second eyelet interference screw. The tamp and thread method is also employed as described above to seat and deliver a second eyelet interference screw and tension the implant as appropriate.

The eyelet interference screw 100, 300, together with an implant 240 sutured to the eyelet member with sutures 232, may be pre-loaded onto the driver 230. As illustrated in FIGS. 13A-13D, the driver 230 may include an interior chamber 234 that houses the implant 240 and sutures 232. In this manner, when eyelet interference screw 100, 300 is decoupled from the driver 230, the implant 240 and sutures 232 are released from the interior chamber 234 and are available for attachment to a second eyelet interference screw 100, 300 for attachment to a second bone tissue 110.

It should be appreciated that all the described embodiments may be custom sized, molded and/or fitted for any clinician based on implant size or anatomy. All the described embodiments may be configured for tissue, tendon, or ligament to be repaired. Moreover, all the described instruments may be formed from any conformable, flexible, rigid, or semi-rigid biocompatible material, e.g., metal, metal alloy, polymer, or the like. The eyelet interference screw 100 may be made at, least partially, from an osteoconductive, osteoinductive, and/or biodegradable material, provided that the material should be strong enough not to break during screw insertion and should provide adequate fixation strength during the healing period. Biodegradable materials may include polymers and copolymers. Examples of suitable materials for making the eyelet interference screw 100, including the eyelet member 120 and the threaded member 109, include, without limitation, polyether ether ketone (PEEK), stainless steel, titanium, cobalt-chromium alloys, shape memory metals, such as nickel titanium alloys, titanium-palladium-nickel alloys, nickel-zirconium-titanium alloys, titanium-niobium alloy, titanium-nickel-niobium alloy, or like biocompatible materials having sufficient hardness, fatigue resistance, corrosion resistance operable to allow for delivery, affixation and anchoring of the repair implant. Any of the embodiments described herein may be used separately from and/or in combination with each other, where practical.

All publications and patent applications mentioned in this specification are herein incorporated by reference to the same extent as if each individual publication or patent application was specifically and individually indicated to be incorporated by reference.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A method of attaching a tissue repair implant to a bone using a threaded interference device, the method comprising:
   (a) creating a blind hole in the bone;
   (b) using a driver, driving the interference device and the tissue repair implant into the blind hole such that a first end of the interference device is inserted into the blind hole; wherein:
      (i) the tissue repair implant comprises a mesh strip, the mesh strip joined to at least one suture; and
      (ii) the mesh strip is coupled to the first end of the interference device;
   (c) using the driver, continue driving the interference device and the mesh strip further into the blind hole such that a threaded portion of the interference device is driven into the blind hole while at the same time the first end of the interference device and the mesh strip are driven further into the blind hole, wherein after driving the interference device and the mesh strip into the blind hole, the mesh strip extends out of the blind hole; and
   (d) securing a free end of the mesh strip that extends out of the blind hole to a second threaded interference device and driving the second threaded interference device and the free end of the mesh strip into a second blind hole.

2. The method of claim 1, wherein the mesh strip driven into the blind hole extends through an opening in the first end of the interference device.

3. The method of claim 2, wherein the mesh strip driven into the blind hole is joined to at least one suture at each end of the mesh strip.

4. The method of claim 2, wherein the mesh strip driven into the blind hole has a modulus of elasticity in the range of between about 12 Mpa and about 116 Mpa.

5. The method of claim 1, wherein the interference device driven into the blind hole comprises a first component and a second component, the first component comprising the first end of the interference device, the second component comprising the threaded portion of the interference device; and wherein a connection between the first component and the second component retains the first component at an end of the second component.

6. The method of claim 5, wherein the connection between the first component and the second component retains the first component at an end of the second component while allowing the first component to rotate relative to the second component.

7. The method of claim 1, wherein a first component comprises an eyelet member with an eyelet opening.

8. The method of claim 1, wherein a second component of the interference device driven into the blind hole further comprises an un-threaded portion.

9. The method of claim 1, wherein the threaded portion of the interference device is selected from the group of a continuous helical thread, discontinuous helical thread, and at least one circumferential ring.

10. The method of claim 1, wherein the tissue repair implant driven into the blind hole passes over the threaded portion of the interference device and extends out of the blind hole.

11. A method of attaching a tissue repair implant to a bone using a threaded interference device, the method comprising:
(a) creating a blind hole in the bone;
(b) using a driver, driving the interference device and the tissue repair implant into the blind hole such that a first end of the interference device is inserted into the blind hole, wherein:
(i) the tissue repair implant comprises a mesh strip, the mesh strip joined to at least one suture;
(ii) the mesh strip is coupled to the first end of the interference device; and
(iii) the interference device comprises a first component and a second component, the first component comprising the first end of the interference device, the second component comprising a threaded portion of the interference device, and a connection between the first component and the second component retains the first component at an end of the second component while allowing the first component to rotate relative to the second component;
(c) using the driver, continue driving the interference device and the mesh strip further into the blind hole such that the threaded portion of the interference device is driven into the blind hole while at the same time the first end of the interference device and the mesh strip are driven further into the blind hole; and
(d) wherein, after driving the interference device and the mesh strip into the blind hole, the mesh strip extends out of the blind hole.

12. The method of claim 11, wherein the mesh strip driven into the blind hole extends through an opening in the first end of the interference device.

13. The method of claim 12, wherein the mesh strip driven into the blind hole is joined to at least one suture at each end of the mesh strip.

14. The method of claim 12, wherein the mesh strip driven into the blind hole has a modulus of elasticity in the range of between about 12 Mpa and about 116 Mpa.

15. The method of claim 11, wherein the mesh strip is attached to a tendon or a ligament.

16. The method of claim 11, further comprising securing a free end of the mesh strip that extends out of the blind hole to a second threaded interference device and driving the second threaded interference device and the free end of the mesh strip into a second blind hole.

17. A method of attaching a tissue repair implant to a bone using a threaded interference device, the method comprising:
(a) creating a blind hole in the bone;
(b) using a driver, driving the interference device and the tissue repair implant into the blind hole such that a first end of the interference device is inserted into the blind hole, wherein:
(i) the tissue repair implant comprises a mesh strip, the mesh strip joined to at least one suture at each end of the mesh strip;
(ii) the mesh strip extends through an opening in the first end of the interference device; and
(iii) the interference device comprises a first component and a second component, the first component comprising the first end of the interference device, the second component comprising a threaded portion of the interference device, and a connection between the first component and the second component retains the first component at an end of the second component while allowing the first component to rotate relative to the second component;
(c) using the driver, continue driving the interference device and the mesh strip further into the blind hole such that a threaded portion of the interference device is driven into the blind hole while at the same time the first end of the interference device and the mesh strip are driven further into the blind hole; and
(d) wherein, after driving the interference device and the mesh strip into the blind hole, the mesh strip extends out of the blind hole.

18. The method of claim 17, further comprising securing a free end of the mesh strip that extends out of the blind hole to a second threaded interference device and driving the second threaded interference device and the free end of the mesh strip into a second blind hole.

* * * * *